United States Patent [19]

Di Bartolomeo

[11] Patent Number: 5,470,587
[45] Date of Patent: Nov. 28, 1995

[54] COMPOSITION AND METHOD FOR TREATMENT OF PATULOUS EUSTACHIAN TUBE SYNDROME AND ATROPHIC RHINITIS

[76] Inventor: Joseph R. Di Bartolomeo, 2420 Castillo St., Santa Barbara, Calif. 03105-4346

[21] Appl. No.: 140,072

[22] PCT Filed: Dec. 10, 1991

[86] PCT No.: PCT/US91/09264

§ 371 Date: May 23, 1994

§ 102(e) Date: May 23, 1994

[87] PCT Pub. No.: WO92/19103

PCT Pub. Date: Nov. 12, 1992

Related U.S. Application Data

[63] Continuation-in-part of Ser. No. 692,486, Apr. 29, 1991, abandoned.

[51] Int. Cl.$^6$ .................................................. A61K 33/14
[52] U.S. Cl. .................................................. 424/661
[58] Field of Search .................................................. 424/661

[56] References Cited

U.S. PATENT DOCUMENTS 1,729,043  9/1924  Kemmerich .................................... 424/661

*Primary Examiner*—Zohreh Fay
*Attorney, Agent, or Firm*—Flehr, Hohbach, Test, Albritton & Herbert

[57] ABSTRACT

A composition and method for the treatment of patulous Eustachian tube syndrome and atrophic rhinitis. The solution is comprised of hydrochloric acid, benzyl alcohol and chlorobutanol, which may be dissolved in propylene glycol, and a pharmaceutically acceptable liquid carrier. The solution is topically applied to the nasal mucosa in appropriate dosage forms for administration intranasally in the form of drops, nasal spray or aerosol.

17 Claims, No Drawings

COMPOSITION AND METHOD FOR TREATMENT OF PATULOUS EUSTACHIAN TUBE SYNDROME AND ATROPHIC RHINITIS

This application is a 371 of PCT/US91/09264 filed on Dec. 10, 1991 and a continuation-in-part of Ser. No. 07/692,486 filed Apr. 29, 1991 now abandoned.

BACKGROUND OF THE INVENTION

1. Technical Field

The present invention relates to the treatment of Patulous Eustachian tube syndrome and atrophic rhinitis.

In humans, sounds of the environment are transmitted to the brain via the external, middle and inner ear structures. The middle ear is an air-filled cavity which contains an eardrum attached to a small set of hearing bones used to transmit sound through the cavity to the inner ear. In order for the eardrum to vibrate freely, the air pressure on both sides of the eardrum should be equal. The Eustachian tube is a narrow passage connecting the middle ear space to the back of the nose (nasopharynx). It is approximately 37 mm long and is slightly hour-glass shaped, flattened anterioposteriorly. The lateral one-third of the Eustachian tube (tympanic segment) is made of bone, while the medial two-thirds (pharyngeal segment) is cartilaginous. A constriction at the junction of the bony and cartilaginous segments, called the isthmus, may be as narrow as 1.0 mm by 1.5 mm. This tube permits the intermittent passage of air to or from the middle ear space to maintain equal pressure on both sides of the eardrum. Normally, this tube is closed, except during swallowing or yawning and the like. In its normal closed state, the Eustachian tube prevents the sounds of chewing and breathing from passing into the middle ear space and interfering with the normal hearing of environmental sounds or conversation.

Disorders of the Eustachian tube and nasal mucosa include:

a. Hyperpatent Disorders of the Eustachian tube

In some individuals the Eustachian tube lumen is abnormally open continuously or intermittently. When the tube is open, it allows the sounds of respiration and speech to pass directly through the patent Eustachian tube to the middle ear sound-receiving mechanism. These individuals are very uncomfortable and frequently complain of a "plugged ear." They also complain of autophony (hearing their own voice while speaking) and of hearing amphoric sounds in their ear—similar to the sound of air being blown across the mouth of an uncapped bottle.

The synonyms for patulous Eustachian tube syndrome include abnormal patent Eustachian tube, semi-patulous Eustachian tube or hyper-patent Eustachian tube.

b. Atrophic Rhinitis

Atrophic rhinitis is a condition in which the nasal mucosa become dry, causing nasal discomfort. The patients usually develop a habit of sniffing in an attempt to continuously clear the nasal mucosa.

2. Background Art

In the past, various medical treatments have been recommended for patulous Eustachian tube syndrome. These include nasal insufflation of boric acid-salicylic acid power, local application of liquid silver nitrate, or diathermy. Surgical procedures have been advocated, including the injection of paraffin, Teflon or collagen into the wall around the Eustachian tube opening. None of these treatments have been consistently successful.

Patients with atrophic rhinitis have attempted to relieve their symptoms by using different ointments, creams or hormones to coat the nasal mucosa. These procedures also have not been consistently successful.

OBJECTS AND SUMMARY OF THE INVENTION

It is a general object of the invention to provide a new and improved composition and method of treatment for patulous Eustachian tube syndrome and atrophic rhinitis.

Another object is to provide a composition and method of the type described which provides the desired therapeutic response through intranasal topical administration in the form of drops, nasal spray or aerosol.

The invention in summary provides a composition and method of treatment for alleviating patulous Eustachian tube syndrome and atrophic rhinitis. A solution of hydrochloric acid, benzyl alcohol, chlorobutanol and a pharmaceutically acceptable liquid carrier in therapeutically effective amounts is applied to the nasal mucosa to obtain the desired therapeutic response.

BEST MODES OF CARRYING OUT THE INVENTION

According to the present invention, a novel composition is provided in a method of treatment to produce closure of the Eustachian tube in the posterior region of the nasal passages for alleviating patulous Eustachian tube syndrome and also to alleviate atrophic rhinitis. The composition is comprised of pharmacologically acceptable salts of the active compounds which are comprised of non-toxic acid addition salts and inorganic acids. The composition includes a pharmaceutically acceptable liquid carrier serving as an inert dilutant, and may also include solvents such as propylene glycol.

The inorganic acid used in the preferred embodiment is hydrochloric acid which is present in the solution in the range of from about 0.25% to about 1% by volume. For example, a 1% hydrochloric acid solution is obtained by adding 3.8 cc reagent grade hydrochloric acid 36% to 97.2 cc distilled water. Benzyl alcohol is then added in an amount sufficient so that it is present in the solution in the range of from about 0.5% to about 5% by volume. Chlorobutanol dissolved in a suitable solvent such as propylene glycol is then added to the solution in a quantity sufficient so that the chlorobutanol is present in the range of from about 0.1% to about 1% and propylene glycol is present in the range of from about 5% to about 25% by volume.

Dosage levels of the active compounds in the composition may be varied so as to obtain a desired therapeutic response for a particular composition and method of administration in accordance with the needs of a particular patient population.

The dilute solution of hydrochloric acid lowers the pH of the nasal mucous and the mucous membrane in the area of the Eustachian tube opening. Typically, the nasal mucous has a pH in the range of approximately 4 to 7. By lowering the pH of the nasal mucous, a response is produced in the mucous membrane and submucosal tissues manifested by congestion of the tissues which are in contact with the typical nasal solution. A solution with a pH in the range of about 0.88 to 3 is effective for this purpose. Hydrochloric acid has been shown to be safe in commercially available nasal spray medications that are sold over the counter and by prescription.

The chlorobutanol is a mild topical anaesthetic and also possesses properties which will preserve the stability of the solution over time. Chlorobutanol has been proven safe as a topical medication in previous nasal solutions. The benzyl alcohol is a mild topical anaesthetic to reduce or eliminate any discomfort associated with the taking of nose drops by some patients. Benzyl alcohol has been approved and recognized for use as a topical anaesthetic in other previous medications.

Once prepared, the solution can be administered into the nose in the form of drops, spray or aerosol or any other method which results in topical application to the nasal mucosa. The form of dosage for intranasal administration includes solutions, suspensions or emulsions of the active compound in the liquid carrier in the form of nose drops, nasal spray or aerosol. Suitable liquid carriers include water, propylene glycol and other pharmaceutically acceptable alcohols. When the dosage form is as a spray or aerosol, the solution is contained in a pressurized container with a liquid propellant such as dichlorodifluoro methane or chlorotrifluoro ethylene. The dosage forms may be sterilized, as required. The dosage forms may also contain adjuvants such as preservatives, stabilizers, emulsifiers or suspending agents, wetting agents, salts for varying the osmotic pressure or buffers, as required. As desired, the solution can also include sweetening, flavoring and perfuming agents.

When the composition is administered in the form of nose drops, the patient sniffs them through the ipsilateral nostril on the side of the ear affected with the disorder. The number of drops administered can be titrated to the needs of the individual patient. The patient can sniff from two to four drops of the solution, and the drops are sniffed back into the nostril so as to deliver the medication to the Eustachian tube opening in the back of the nose. Administration of the drops may be repeated again in four to six hours. As desired, the daily dose may be divided into multiples doses over a 24-hour period. The medication is taken while awake and ambulatory. It is not required when the patient is lying down or sleeping. The following examples are set forth to illustrate the invention.

EXAMPLE I

A 36-year-old female had a history of autophony which occurred throughout the day several days a week, especially during and after exercise. The patient was treated with nose drops comprising an aqueous solution of 0.5% hydrochloric acid, 1.0% chlorobutanol and 1.0% benzyl alcohol, with the solution having a pH of 1. Three drops of the solution were sniffed into the nostril on the side of the abnormal Eustachian tube. The drops were taken approximately two hours after arising from sleep, and repeated again six hours later. Excellent results were achieved with the patulous Eustachian tube syndrome completely relieved, and no adverse side effects were noted. The treatment was intermittently required approximately every two months.

EXAMPLE II

A 52-year-old male suffered from a unilateral hyperpatent Eustachian tube syndrome which occurred approximately two days a weeks and about three weeks each month. A composition comprising an aqueous solution of 1.0% hydrochloric acid, 1.0% chlorobutanol and 1.0% benzyl alcohol with a pH of 0.88 was administered in a dosage of two drops for each treatment. The patient sniffed the drops into the ipsilateral nostril approximately three hours after arising in the morning. This treatment was repeated on subsequent mornings when symptoms were present. The results were excellent in that the Eustachian tube functioned normally and there were no adverse side effects. Approximately every six months the patient requires the treatment with the nose drops administered for about one week.

EXAMPLE III

A 56-year-old male patient suffered from atrophic rhinitis with crusting. A composition comprising an aqueous solution of 1.0% hydrochloric acid, 1.0% chlorobutanol and 1.0% benzyl alcohol with a pH of 0.9 was administered in a dosage of two drops for each treatment. The medication was taken several hours after arising and again six hours later. This was repeated for seven days. After two weeks the crusting diminished and the patient experienced less dryness, demonstrating a satisfactory alleviation of his symptoms.

Administration of the solution in accordance with the invention produces sufficient congestion of the mucous membranes around the lumen of the Eustachian tube to accomplish adequate closure. When the membrane around the Eustachian tube lumen swells enough to close the opening, the disturbing sensation of "plugged ear," autophony or annoying amphoric sounds of the patient's breathing are eliminated or controlled. The treatment is safe, inexpensive, has predictable results, and the amount administered can be titrated according to the individual needs of the patient.

While the foregoing embodiments are at present considered to be preferred, it is understood that numerous variations and modifications may be made therein by those skilled in the art and it is intended to cover in the appended claims all such variations and modifications as fall within the true spirit and scope of the invention.

What is claimed is:

1. A method of treating patulous Eustachian tube syndrome, comprising applying to a person's nasal mucosa a solution comprised of hydrochloric acid, a pharmaceutically acceptable mild topical anaesthetic selected from the group consisting of benzyl alcohol and chlorobutanol, and a pharmaceutically acceptable liquid carrier in therapeutically effective amounts to treat patulous Eustachian tube syndrome.

2. A method according to claim 1 in which the solution is topically applied to the nasal mucosa.

3. A method according to claim 2 in which the solution is applied in drops into the nose.

4. A method according to claim 2 in which the solution is applied in an aerosol into the nose.

5. A method according to claim 2 in which the solution is applied in a spray into the nose.

6. A method according to claim 1 in which the liquid carrier is water.

7. A method according to claim 1 in which the solution has a pH in the range of about 0.88 to 3.

8. A method according to claim 1 in which the hydrochloric acid is present in the carrier at a concentration in the range of from about 0.25% to about 1% by volume, the benzyl alcohol is present in the carrier at a concentration in the range of from about 0.5% to about 5.0% by volume, and the chlorobutanol is present in the carrier at a concentration in the range of from about 0.1% to about 1.0% by volume.

9. A method according to claims 1 or 8 in which the solution further comprises propylene glycol in an effective amount to dissolve the chlorobutanol.

10. A composition for treating patulous Eustachian tube syndrome, comprising a solution of hydrochloric acid, a pharmaceutically acceptable mild topical anaesthetic selected from the group consisting of benzyl alcohol and chlorobutanol, a pharmaceutically acceptable liquid carrier in therapeutically effective amounts to treat patulous Eustachian tube syndrome, said solution being devoid of vasoconstricting agents and astringent agents, and said solution having a pH in the range of about 0.88 to 3.

11. A composition according to claim 10 in which the hydrochloric acid is present in the carrier at a concentration in the range of from about 0.25% to about 1.0% by volume.

12. A composition according to claim 10 in which benzyl alcohol is present in the carrier at a concentration in the range of from about 0.5% to about 5.0% by volume.

13. A composition according to claim 10 in which the chlorobutanol is present in the carrier at a concentration in the range of from about 0.1% to about 1.0% by volume.

14. A composition according to claim 10 in which the liquid carrier is water.

15. A composition according to claim 10 in which the hydrochloric acid is present in the carrier at a concentration in the range of from about 0.25% to about 1.0% by volume, the benzyl alcohol is present in the carrier at a concentration in the range of from about 0.5% to about 5.0% by volume, and the chlorobutanol is present in the carrier at a concentration in the range of from about 0.1% to about 1.0% by volume.

16. A composition according to claims 10 or 15 in which the solution further comprises propylene glycol in an effective amount to dissolve the chlorobutanol.

17. A composition according to claim 15 in which the solution further comprises propylene glycol at a concentration in the range of from about 5% to about 2.5% by volume.

\* \* \* \* \*